United States Patent [19]

Kinast

[11] Patent Number: 4,500,716
[45] Date of Patent: Feb. 19, 1985

[54] INTERMEDIATE PRODUCTS FOR THE PREPARATION OF Z-CEPHALOSPORINS

[75] Inventor: Günther Kinast, Wuppertal, Fed. Rep. of Germany

[73] Assignee: Bayer Aktiengesellschaft, Leverkusen, Fed. Rep. of Germany

[21] Appl. No.: 438,189

[22] Filed: Nov. 1, 1982

[30] Foreign Application Priority Data

Nov. 19, 1981 [DE] Fed. Rep. of Germany ....... 3145727

[51] Int. Cl.$^3$ ........................................... C07D 277/48
[52] U.S. Cl. ...................................... 548/196; 544/22; 544/27; 544/28
[58] Field of Search .......................................... 548/196

[56] References Cited

U.S. PATENT DOCUMENTS

| | | | |
|---|---|---|---|
| 3,483,216 | 12/1969 | Woodward | 548/196 |
| 4,008,246 | 2/1977 | Ochiai et al. | 548/196 |
| 4,416,880 | 11/1983 | Boberg et al. | 542/453 |

Primary Examiner—Paul M. Coughlan, Jr.
Attorney, Agent, or Firm—Sprung, Horn, Kramer & Woods

[57] ABSTRACT

Highly active substantially pure Z-isomers of cephalosporins are produced by the following synthesis:

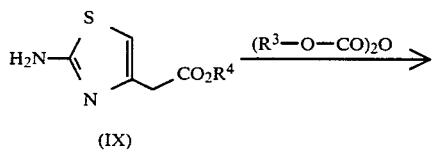

(IX)

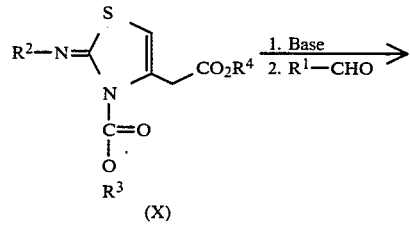

(X)

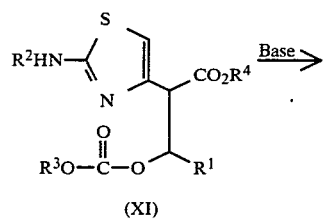

(XI)

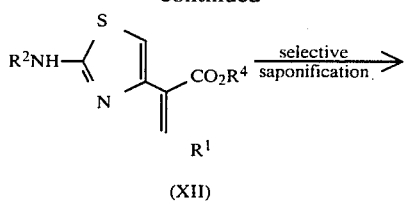

(XII)

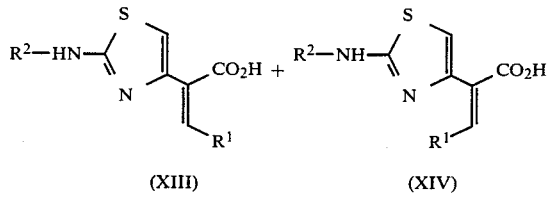

(XIII)          (XIV)

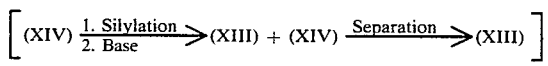

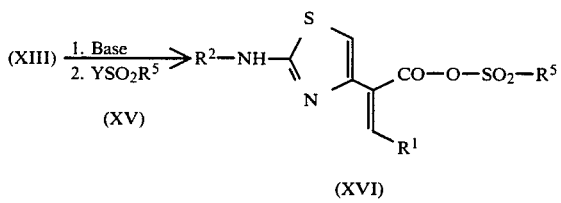

(XV)

(XVI)

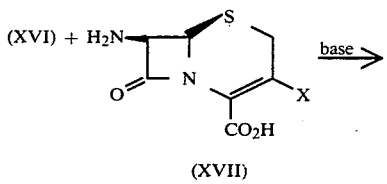

(XVII)

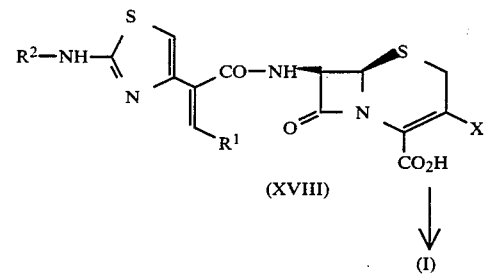

(XVIII)

↓

(I)

in which
R$^1$, R$^4$ and R$^5$ ae various organic radicals,
R$^2$ is alkoxycarbonyl,
Y is Cl, Br or —O—SO$_2$—R$^5$, and
X is a conventional cephalosporin substituent.

Many of the intermediates are new, especially in pure Z-form.

8 Claims, No Drawings

INTERMEDIATE PRODUCTS FOR THE PREPARATION OF Z-CEPHALOSPORINS

The invention relates to certain intermediate compounds, to processes for their production and to their use for the preparation of certain cephalosporins.

Cephalosporins of the general formula

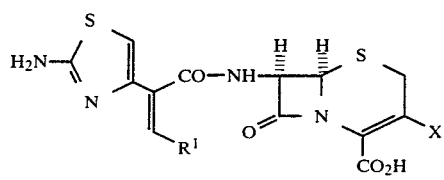
(I)

in which $R^1$ denotes an alkyl or aryl radical, are mentioned in U.S. Ser. No. 304,280, filed Sept. 21, 1981, now U.S. Pat. No. 4,416,880. These compounds have a broad antibacterial activity both against Gram-negative and also against Gram-positive bacteria.

According to the process mentioned in this relatively old application, the compounds of the formula (I) are prepared according to the following reaction scheme:

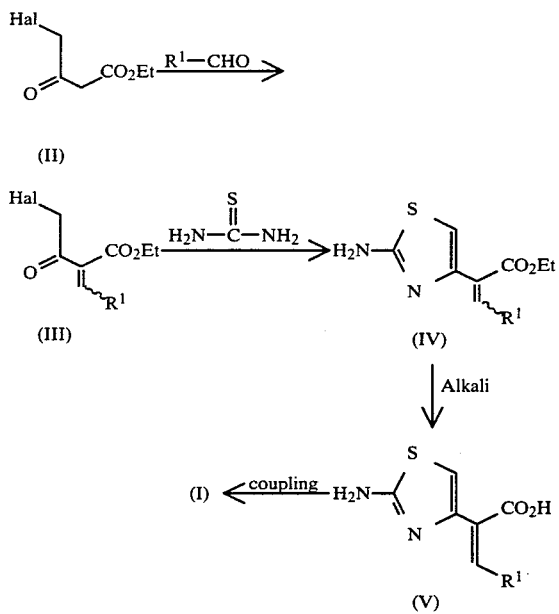

However, this process leads only to unsatisfactory yields of compounds of the formula (I) in which $R^1$ denotes an alkyl radical. Thus, for example, for the case in which $R^1$ denotes an isopropyl radical, on reaction of the compound of formula (III) with thiourea, in addition to the desired compound of formula (IV), the products of the following formulae

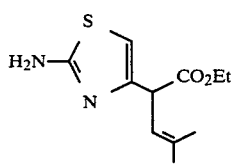
(VI)

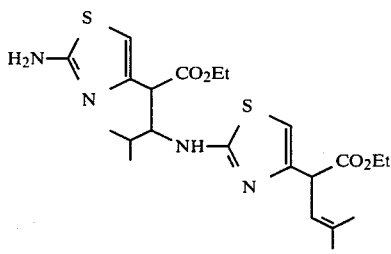
(VII)

are obtained as by far the largest fraction, due to deconjugation of the double bond and to Michael addition.

Furthermore, when $R^1$ denotes an alkyl radical, when the processes described in the application mentioned (with for example, hydroxybenzotriazole/DCC) are used for the coupling of the acids of formula (V) to the 7-aminocephalosporanic acids to give the products of the formula (I), isomerization of the double bond to give the products of the formula:

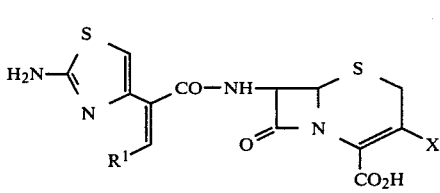
(VIII)

occurs to a large extent. However, the compounds of the formula (VIII) generally show only about 1/10 of the biological activity of the compounds of the formula (I).

A process for the preparation of the compounds of the formula (I) has now been found, which proceeds via new intermediate products, and which does not have the abovementioned disadvantages.

According to the present invention we therefore provide a process for the production of a compound of the general formula

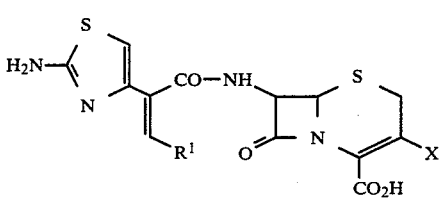
(I)

in which
  $R^1$ represents an optionally substituted alkyl, cycloalkyl, aryl or heterocyclyl radical and
  X represents a radical suitable as a cephalosporin substituent,
in which
  (a) a compound of the general formula

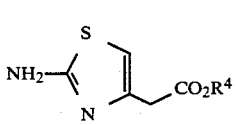
(IX)

is reacted with a pyrocarbonic acid ester of the general formula $$R^3-O-CO-O-CO-O-R^3$$

in which
R$^3$ and R$^4$ can be the same or different and denote an optionally substituted alkyl, cycloalkyl, alkenyl, cycloalkenyl, aryl or heterocyclyl radical, there being at least one carbon atom separating heteroatoms as substituents of the radicals and double bonds in the alkenyl and cycloalkenyl radicals from the oxycarbonyl group,
(b) the product of the general formula

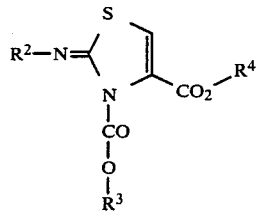

(X)

in which
R$^2$ denotes CO$_2$R$^3$, and
R$^3$ and R$^4$ have the meanings given above, thus obtained is initially reacted with a suitable base and then with an aldehyde of the general formula R$^1$—CHO, in which R$^1$ has the meaning given above, to give a compound of the general formula

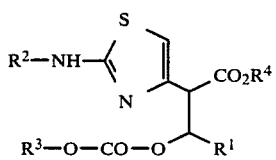

(XI)

in which R$^1$, R$^2$, R$^3$ and R$^4$ have the meanings given above,
which
(c) is then reacted with a base to give a compound of the general formula

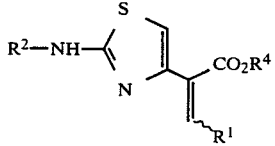

(XII)

in which R$^1$, R$^2$ and R$^4$ have the meanings given above,
(d) the Z-acid of the general formula

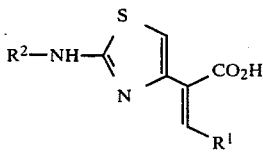

(XIII)

in which R$^1$ and R$^2$ have the meanings given above, is then obtained from the compound of formula (XII) by separation of the Z and E isomers and subsequent saponification or by selective saponification, and (e) the Z-acid of formula (XIII) is then reacted with a compound of the general formula $$Y-SO_2-R^5$$

in which
Y denotes a chlorine or bromine atom or —O—SO$_2$—R$^5$,
and
R$^5$ denotes an optionally substituted alkyl, alkenyl, cycloalkyl, cycloalkenyl, aryl or heterocyclyl radical,
to give a compound of the general formula

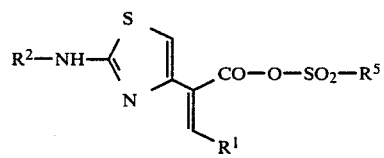

(XVI)

which R$^5$ and Y have the meanings given above,
(f) is then coupled with a cephalosporanic acid of the general formula

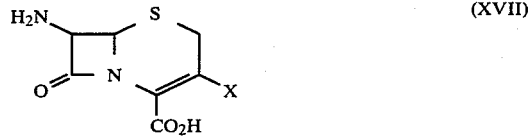

(XVII)

in which X has the meaning given above,
and
(g) the protective group R$^2$ is then split off.
The present invention further provides, as new compounds, the compounds of the general formula

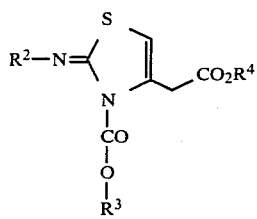

(X)

in which R$^2$, R$^3$ and R$^4$ have the meanings given above.
According to the present invention we further provide a process for the production of compounds of formula (X) in which a compound of formula (IX), as defined above, is reacted with a pyrocarbonic acid ester of formula (IXa), as defined above, in a solvent for the reactants.
The present invention further provides as new compounds, the compounds of the general formula

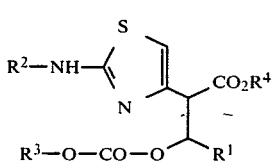

(XI)

in which $R^1$, $R^2$, $R^3$ and $R^4$ have the meanings given above, and $R^1$ represents an optionally substituted alkyl, cycloalkyl, aryl or heterocyclyl radical.

According to the present invention we further provide a process for the production of a compound of formula (XI), in which a compound of formula (X), as defined above, is reacted in a solvent for the reactant at a low temperature, with a base and then with an aldehyde of the general formula $R^1$—CHO in which $R^1$ has the meaning given above.

The present invention yet further provides, as new compounds, the compounds of the general formula

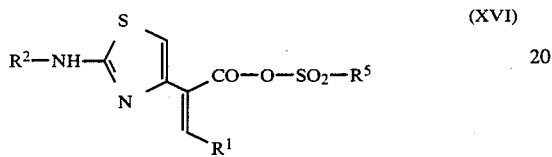

(XVI)

in which $R^1$ and $R^2$ have the meanings given above, and $R^5$ represents a fluorine atom, an optionally substituted alkyl, alkenyl, cycloalkyl, cycloalkenyl, aryl, or heterocyclyl radical.

According to the present invention we yet further provide a process for the production of a compound of formula (XVI), in which a compound of the general formula

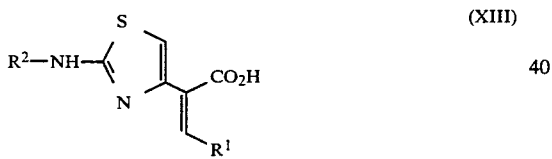

(XIII)

in which $R^1$ and $R^2$ have the meanings given above, is reacted with a compound of the general formula $$Y—SO_2—R^5 \quad (XV)$$

in which

Y denotes a chlorine or bromine atom or —O—SO$_2$—$R^5$, and $R^5$ has the meaning given above.

The process according to the present invention for the production of compounds of formula (I) may be summarized in the following reaction scheme:

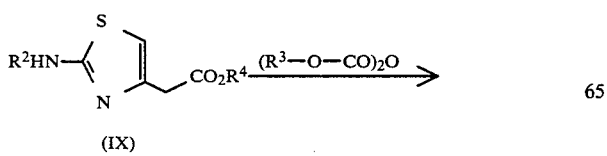

-continued

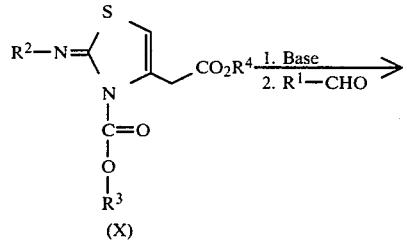

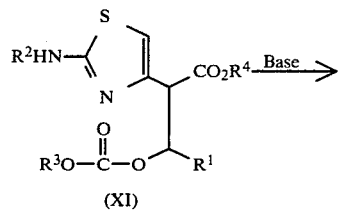

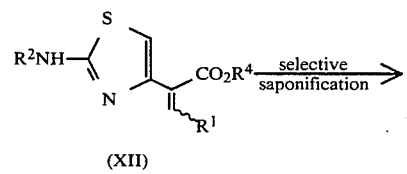

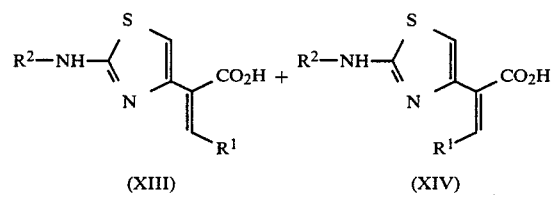

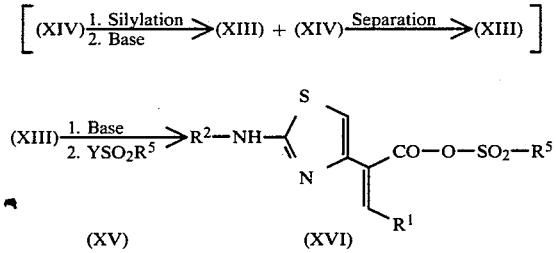

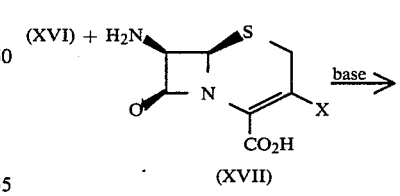

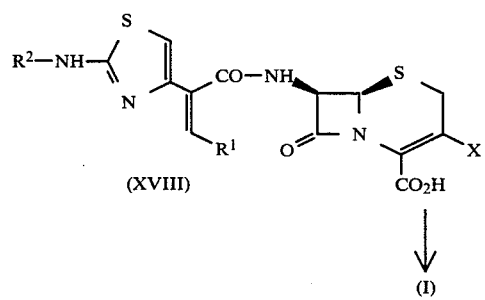

Further details of the reaction steps for the production of compounds of formula (I) are given later in the specification.

Particularly preferred compounds of formula (X) according to the invention are those in which, $R^2$ denotes —OC—O(CH$_3$)$_3$ $R^3$ denotes C(CH$_3$)$_3$ and $R^4$ denotes optionally substituted alkyl radical with 1 to 15 carbon atoms, an optionally substituted alkenyl radical with 3 to 15 carbon atoms, an optionally substituted cycloalkyl radical with 3 to 10 carbon atoms, an optionally substituted cycloalkenyl radical with 5 to 10 carbon atoms, an optionally substituted aryl radical with 1 to 3 rings or an optionally substituted heterocyclyl radical with 1 to 3 rings, which can contain up to 5 hetero atoms selected from nitrogen, sulphur and oxygen.

Especially preferred compounds of formula (X) according to the invention are those in which $R^2$ denotes a tert.-butoxycarbonyl radical, $R^3$ denotes a tert.-butyl radical, and $R^4$ denotes a methyl, ethyl, tert. butyl or trimethylsilyl ethyl radical.

The alkyl, alkenyl, cycloalkyl and cylcoalkenyl, radicals mentioned can be substituted by alkyl radicals with 1 to 4 carbon atoms, O-alkyl radicals with 1 to 4 carbon atoms, halogen (preferably chlorine), optionally substituted phenyl radicals, C≡N and tri-(C$_1$ to C$_5$ alkyl)silyl.

All the aryl and heterocyclyl radicals, including the phenyl radicals mentioned, can be substituted by alkyl, O-alkyl, S-alkyl, alkyloxycarbonyl, halogen and phenyl radicals, it being possible for all alkyl radicals to have 1 to 4 carbon atoms, and by nitro and C≡N.

When the radicals $R^3$ and/or $R^4$ are substituted, preferably by the abovementioned substituents, they can carry 1 to 5, preferably 1 or 2, substituents.

It is particularly advantageous for the process when $R^2$ denotes a protective group which is stable to base and removable in acid, such as tert.-butoxy-carbonyl, and when $R^4$ denotes a radical which is saponifiable by base, such as methyl or ethyl.

The compounds of the formula (IX) used in the process according to the invention for the production of compounds of formula (X) are known in themselves (see, for example, E. Campaine and T. P. Selby, J. Heterocycl. Chem. 17 (1980)).

Particularly suitable solvents for the production of compounds of formula (X) are aprotic polar solvents such as acetonitrile, dimethylformamide, hexamethylphosphoric acid triamide or dimethyl sulphoxide, particularly the latter two. The reaction takes place particularly advantageously at room temperature or at lower temperatures, for example, between 10° and −50° C., the components generally being allowed to react with one another for 1 to 7 days. The pyrocarbonic acid ester of formula (IXa) is generally employed in 2 to 2.5 mol-equivalents.

Other solvents, higher temperatures or acylation catalysts, such as 4-dimethylaminopyridine, strongly favor the formation of the undesired products of the formula

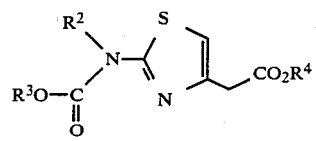

(XIX)

In the process according to the invention for the preparation of the novel compounds of the formula (XI), generally the compound of the formula (X) is treated with 1 to 1.1 equivalents of a base in a solvent for the reactants at a low temperature, and then 1 to 1.2 equivalents of an aldehyde of the formula $R^1$—CHO is added.

Solvents which may be used for this reaction are, for example, dimethylformamide, diethyl ether, tetrahydrofuran or toluene—preferably tetrahydrofuran—and bases which may be used are alcoholates, hydrides, amides or organometallics—preferably potassium tert.-butylate, lithium diisopropylamide and butyllithium. To carry out the reaction, the base is generally added, at −50° to −80° C., to a solution of the compound of formula (X), and then the aldehyde is added at −50° to −60° C., and the mixture is stirred at −50° to −60° C. for about 12 hours. To isolate the product of the formula (XI), the mixture may be neutralized and worked up.

Preferred compounds of the formula (XI) are those in which $R^2$ to $R^4$ have the meanings given above, and $R^1$ denotes an optionally substituted alkyl radical with 1 to 15 carbon atoms, an optionally substituted cycloalkyl radical with 3 to 10 carbon atoms, an optionally substituted carbocyclic or heterocyclic aryl radical with 1 or 2 rings or an optionally substituted heterocyclic radical with 1 to 3 rings, which can contain up to 5 heteroatoms selected from nitrogen, sulphur and oxygen atoms.

Suitable substituents for alkyl and cycloalkyl are alkyl radicals with 1 to 6 carbon atoms, O-alkyl radicals with 1 to 6 carbon atoms, S-alkyl radicals with 1 to 6 carbon atoms, N-alkyl radicals with 1 to 6 carbon atoms, alkyloxycarbonyl radicals with 1 to 6 carbon atoms and optionally substituted phenyl radicals.

All the aryl and heterocyclyl radicals, including the phenyl radicals mentioned, can be substituted by alkyl, O-alkyl, S-alkyl, alkyloxycarbonyl, halogen, preferably chlorine, and phenyl radicals, it being possible for all the alkyl radicals to carry 1 to 6 carbon atoms.

If $R^1$ represents a substituted (preferably by the abovementioned substituents) radical, 1 to 5, preferably 1 or 2, substituents are preferred.

It is particularly preferred that $R^1$ denotes an alkyl radical with 1 to 10 carbon atoms or a cycloalkyl radical with 3 to 10 carbon atoms, which, in each case, can be substituted by 1 or 2 alkyl radicals with 1 to 6 carbon atoms and/or 1 or 2 phenyl radicals.

It is unnecessary to isolate the compounds of the formula (XI) in carrying out the process according to the invention for the preparation of the compounds of the formula (I). On the contrary, it is advantageous to convert the former directly into the compounds of the formula (XII) in situ. For this purpose, it is generally sufficient to allow the mixture after addition of the aldehyde $R^1$—CHO to warm to room temperature and to stir it overnight at room temperature. If the elimination reaction of the compound of formula (XI) to give the compound of formula (XII) is not then complete, 1 to 1.2 equivalents of a base (such as a hydride, an alcoholate or an amide—particularly potassium tert.-butylate) is added and the mixture stirred at room temperature for about 10 hours.

If, on the other hand, the compounds of the formula (XI) had been previously isolated, for the preparation of the compounds of the formula (XII), 1.1 to 2.2 equivalents of a base are added to a solution of the compounds of the formula (XI) in a suitable solvent. The solvent and the base used can be those mentioned for the reaction of the compound of formula (X) to give the compound of formula (XI), preferably tetrahydrofuran and potassium tert.-butylate.

The compounds of the formula (XII) are obtained as mixtures of E/Z isomers, which, for example, may be separated by recrystallization or by column chromatography on silica gel.

$R^1$, $R^2$ and $R^4$ in the compounds of the formula (XII) have the same meanings as in the compounds of formula (XI).

For the preparation of the Z-carboxylic acids of the formula (XIII), the Z-esters, which can be obtained by separation of the mixture of the E/Z isomers of the esters of the formula (XII), can be saponified. However, it is more favorable for carrying out the process for the preparation of the compounds of the formula (I) to saponify selectively the mixture of E/Z isomers of the esters of the formula (XII) in such a manner that the E-esters are first converted, under mild conditions, into the E-carboxylic acids of the formula (XIV), and separated out and then the remaining Z-esters, in which the ester group is more sterically shielded, are saponified under more drastic conditions to give the Z-carboxylic acids of the formula (XIII).

The mild conditions for saponification, which lead to the E-carboxylic acids (XIV), are, for example, ethanol/2N sodium hydroxide solution/room temperature/24 hours. It is advantageous to carry out the saponification in such a manner that, after conversion of the compounds of the formula (XI) into the compounds of the formula (XII), 2N sodium hydroxide solution is directly added to the reaction mixture and this is stirred at room temperature or with slight heating until the E-esters are saponified. Thereafter, the Z-esters are removed from the mixture by extraction under alkaline conditions and they are saponified under more drastic conditions.

More drastic conditions for saponification are, for example, ethanol/2N sodium hydroxide solution/24 hours reflux-possibly even more concentrated sodium hydroxide solution or higher-boiling solvents, for example dioxane.

The desired Z-carboxylic acids of the formula (XIII) and the E-carboxylic acids of the formula (XIV) are obtained in this manner. The latter may be converted back, after conversion into the silyl esters, for example, with bistrimethylsilylacetamide, in a suitable solvent, for example, diethyl ether or tetrahydrofuran, with a base, such as potassium tert.-butylate and subsequent hydrolysis with dilute acid into a mixture of the E-carboxylic acids of the formula (XIV) and the Z-carboxylic acids of the formula (XIII).

The Z-carboxylic acids of the formula (XIII) may be isolated in pure form from this mixture of E/Z isomers, for example by crystallization or by separation on an ion exchanger. Separation with the aid of ion exchangers is simple, since the Z-carboxylic acids of the formula (XIII) have a much higher acidity than the E-carboxylic acids of the formula (XIV). Thus, the E-carboxylic acids of the formula (XIV) are eluted just with methanol from weakly basic ion exchangers, whereas, in contrast, the Z-carboxylic acids of the formula (XIII) are only eluted after addition of electrolytes, for example, 2N sodium hydroxide solution. Weakly basic ion exchangers are to be understood as including those ion exchangers in solid or liquid form which contain tertiary amino groups, for example Lewatit MP 62.

$R^1$ and $R^2$ in the compounds of the formula (XIII) and (XIV) have the same meanings as in the compound of formula (XII). In addition, $R^2$ can be a hydrogen atom, if, before saponification, $R^2$ in the compounds of the formula (XII) was a protective group saponifiable by alkali (such as a methyloxycarbonyl group). However, it is more advantageous for carrying out the process for the preparation of the compounds of the formula (I) if $R^2$ is a protective group which is stable under the conditions of saponification, preferably tert.-butyloxycarbonyl.

A large number of methods, which in the last analysis are derived from peptide chemistry, are known in cephalosporin chemistry for coupling carboxylic acids to 7-aminocephalosporanic acids. However, these methods fail on attempting to form the amide bond between the Z-carboxylic acids of the formula (XIII) and the cephalosporanic acids of the formula (XVII), or they only lead to very poor yields, particularly when $R^1$ is an alkyl radical. The reasons for this are to be found in the large steric hindrance of the carboxyl group in the carboxylic acids of the formula (XIII) by the radical $R^1$ and in the pronounced tendency of the radical $R^1$ to isomerize into the E-form after activation of the carboxyl function, for example, conversion into the acid chloride. Then, after reaction with the 7-aminocephalosporanic acids of the formula (XVII), the desired compounds of the formula (XVIII) are not obtained, but rather the compounds of the formula

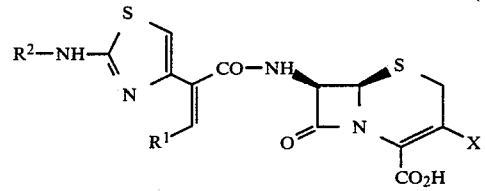

(XXI)

or mixtures of the two.

It has now been found that the Z-carboxylic acids of the formula (XIII) can be activated in a simple, mild and inexpensive manner and without the abovementioned disadvantages by converting them into the mixed anhydrides of the formula (XVI) at low temperatures.

As indicated previously, these compounds of the formula (XVI) are new and form a further subject of the present invention.

In these compounds $R^5$, when an optionally substituted alkyl, alkenyl, cycloalkyl, cycloalkenyl, aryl or heterocyclyl radical, can be substituted by a substituent selected from halogen, alkyl, aryl, O-alkyl, S-alkyl, CN, alkoxycarbonyl and nitro.

Especially preferred compounds of formula (XVI) are those in which $R^5$ denotes an alkyl radical with 1 to 10 carbon atoms, which is optionally substituted by fluorine, chlorine, CN, phenyl, alkyloxycarbonyl, alkyloxy or alkyl (it being preferred for the alkyl groups of these substituents to carry 1 to 4 carbon atoms); or denotes a phenyl radical, which is optionally substituted by fluorine, chlorine, bromine, CN, alkyl, alkyloxy, alkylthio and alkyloxycarbonyl (it being preferred for the alkyl groups of these substituents to carry 1 to 4 carbon atoms), and nitro, trifluoromethyl and phenyl.

When $R^5$ is substituted, there are preferably 1 to 3 substituents, preferably those mentioned, present.

In very particularly preferred compounds of formula (XVI) $R^5$ represents a methyl or p-tolyl radical.

This type of mixed anhydrides of the formula (XVI) is preferably prepared by dissolving the carboxylic acid of formula (XIII) and a suitable amine in equimolar amounts in a suitable solvent and allowing them to react with 1 to 1.05 equivalents of a sulphonic acid derivative of the formula (XV).

Suitable solvents here are any of the solvents which are stable under the reaction conditions (such as diethyl ether, tetrahydrofuran, acetonitrile, acetone, methylene chloride, chloroform or dimethylformamide).

Suitable amines are tertiary amines (such as triethylamine or tributylamine) and also sterically hindered secondary amines (such as diisopropylamine).

The reactions can be carried out at a temperature between $-80°$ C. and room temperature, low temperatures preventing isomerization of the substituents on the double bond. The reactions are advantageously carried out at $-20°$ to $-50°$ C. with a duration of reaction of 10 minutes to hours.

The compounds of the formula (XVI) can be isolated by using, for example, tetrahydrofuran as the solvent and triethylamine as the base, filtering off under suction the triethylamine hydrochloride formed and distilling of the solvent in vacuo. However, it is more advantageous to react the solutions of the compounds of the formula (XVI) obtained directly with the cephalosporanic acids of the formula (XVII). For this purpose, the cephalosporanic acids of the formula (XVII) are dissolved in a suitable solvent with 2 to 4 equivalents of an amine, the solution is pre-cooled to the desired subsequent reaction temperature and this solution at this temperature is added to the solution of the compound of formula (XVI) described above. In order to prevent isomerization of the radical $R^1$ in reaction products of the formula (XVIII), the reaction is advantageously carried out at $-60°$ to $-30°$ C. and the mixture is allowed to reach room temperature overnight.

The amines and solvents mentioned for the preparation of the compounds of the formula (XVI) can be to dissolve the cephalosporanic acids of the formula (XVII). If solutions with satisfactory concentration of the cephalosporanic acids of the formula (XVII) cannot be obtained in this manner, it is obviously also possible to employ the readily soluble esters of the compounds of formula (XVII), which are sufficiently well-known from cephalosporin chemistry (such as silyl, tert.-butyl or diphenylmethyl esters).

After work-up, the compounds of formula (XVIII) are obtained, in which $R^1$ and $R^2$ exhibit the meanings mentioned for the compounds of formula (XVI) and X represents a group suitable as a cephalosporin substituent for example denotes hydrogen, $C_1$ to $C_4$ alkyl, halogen, $C_1$ to $C_4$ alkoxy, hydroxymethyl, formyloxymethyl, ($C_1$ to $C_4$ alkyl)-carbonyloxymethyl, aminocarbonyloxymethyl, pyridiniummethyl, 4-carbamoylpyridiniummethyl or heterocyclylthiomethyl ("heterocyclyl" preferably representing a radical of the formula

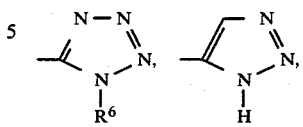

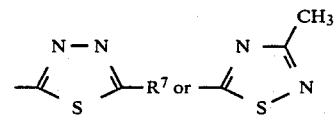

in which
$R^6$ denotes hydrogen, methyl, 2-dimethylaminoethyl, carboxymethyl or sulphomethyl and
$R^7$ denotes hydrogen or methyl).

Preferred compounds of formula (XVIII) are those in which X denotes hydrogen, chlorine, methoxy, hydroxymethyl, acetyloxymethyl, aminocarbonyloxymethyl, pyridiniummethyl,

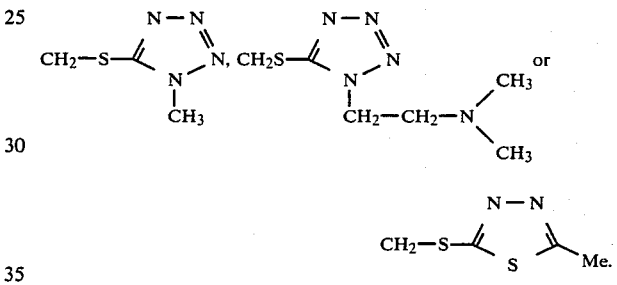

The compound of the formula (I), in which $R^1$ and X exhibit the meaning mentioned for the compounds of formula (XVIII), is obtained from the compounds of formula (XVIII) after splitting off the protective group $R^2$. As already mentioned for the compounds of formula (X), it is extremely advantageous for the complete reaction sequence for the preparation of the compounds of formula (I) to be carried out directly from the compounds of formula (X) if $R^2$ is a protective group stable in base which may be selectively split off, such as tert.-butyloxycarbonyl (split off with trifluoroacetic acid).

The process according to the present invention and the production of compounds according to the invention are illustrated by the following examples:

EXAMPLE 1

Ethyl 2-tert.-butoxycarbonylimino-3-tert.-butoxycarbonyl-4-thiazolin-4-ylacetate 186 g (1 mol) of ethyl 2-aminothiazol-4-ylacetate, 300 ml of dimethyl sulphoxide and 500 g (2.3 mols) of 98% di-tert.-butyl pyrocarbonate are stirred at room temperature for 7 days. Then 3.5 l of ice-water are added with ice cooling at max. 20° C., the mixture is stirred for 30 minutes, the precipitate is filtered off under suction, is washed with 2 l of water and is taken up in 2 l of methylene chloride. The water is separated off, the methylene chloride phase is dried over $Na_2SO_4$ and concentrated on a rotary evaporator. The oil obtained is taken up immediately (before crystallization starts) for crystallization in 2 l of petroleum ether.

Yield 302 g (78%), melting point 90° C.

EXAMPLE 2

Methyl 2-tert.-butoxycarbonylimino-3-tert.-butoxycarbonyl-4-thiazolin-4-ylacetate is prepared from methyl 2-aminothiazol-4-ylacetate analogy to Example 1.

Yield 67%, melting point 67°–69° C.

EXAMPLE 3

Ethyl 2-ethoxycarbonylimino-3-ethoxycarbonyl-4-thiazolin-4-ylacetate is prepared from ethyl 2-aminothiazol-4-ylacetate and diethyl pyrocarbonate in analogy to Example 1.

Yield 71%, melting point 102° C.

EXAMPLE 4

Tert.-butyl 2-tert.-butoxycarbonylimino-3-tert.-butoxycarbonyl-4-thiazolin-4-ylacetate 157 g (0.5 mol) of tert.-butyl 2-aminothiazol-4-ylacetate, 150 ml of dimethyl sulphoxide and 260 g (1.2 mols) of 98% di-tert.-butyl pyrocarbonate were reacted in analogy to Example 1.

Yield 62%.

EXAMPLE 5

Trimethylsilylethyl 2-aminothiazol-4-ylacetate 11.2 g (15.8 ml, 0.1 mol) of trimethylsilylethanol, 100 mg of 4-dimethylaminopyridine and 11.4 g of dicyclohexylcarbodiimide are added at room temperature to 7.9 g (0.05 mol) of 2-aminothiazol-4-ylacetic acid in 50 ml of acetonitrile and the mixture is stirred for 2 days. The precipitated urea is then filtered off under suction, washed with ether, the washings are concentrated on a rotary evaporator and the residue is taken up in ether and the ethereal solution is washed with 0.5N hydrochloric acid and with $NaHCO_3$ solution, dried over $MgSO_4$ and concentrated on a rotary evaporator. After concentration of the solution and addition of petroleum ether, the desired ester crystallizes out.

Yield 2.8 g.

EXAMPLE 6

Trimethylsilylethyl 2-tert.-butyloxycarbonylimino-3-tert.-butoxycarbonyl-4-thiazolin-4-ylacetate is prepared from trimethylsilyl 2-aminothiazol-4-ylacetate in analogy to Example 1.

Yield 50%.

EXAMPLE 7

Ethyl 1-(2-tert.-butoxycarbonylaminothiazol-4-yl)-2-tert.-butoxycarbonyloxypropanecarboxylate 11.2 g (0.03 mol) of ethyl 2-tert.-butoxycarbonylimino-3-tert.-butoxycarbonyl-4-thiazolin-4-ylacetate were dissolved in 80 ml of anhydrous tetrahydrofuran, and, under nitrogen at −50° to −60° C., 20 ml (0.032 mol) of a 15% strength solution of n-butyllithium in n-hexane was added, followed by 1.91 ml (0.034 mol) of acetaldehyde. The mixture was stirred at −50° to −60° C. for 2 hours, then 30 ml of a 10% strength solution of citric acid in water was added and the mixture was allowed to warm to room temperature. To work up, the tetrahydrofuran was distilled off at room temperature in vacuo, the residue was extracted with methylene chloride, the organic extract was dried over $Na_2SO_4$ and the solvent was distilled off. 10.8 g of an oil was obtained which, according to NMR, was a mixture of diastereomers (TLC: cyclohexane/ether 1:1).

EXAMPLE 8

Ethyl 1-(2-tert.-butoxycarbonylaminothiazol-4-yl)-1(E,Z)-propenecarboxylate

The mixture is prepared as indicated in Example 7. However, after addition of the acetaldehyde, it is allowed to warm to room temperature, is then stirred overnight and is only then worked up as indicated in Example 7. 9.2 g of an oil is obtained which, according to NMR and TLC (cyclohexane/ether 1:1, Z isomer runs higher) is an approximately 1:1 mixture of E/Z isomers. The two compounds can be separated on silica gel 60 (mobile phase cyclohexane/ether 1:1).

Z isomer:

$^1$H-NMR (250 MHz, $CDCl_3$): $\delta = 10.5$ (bs; 1H, NH), 6.95 (s; 1H, S-CH), 6.88 (q; J=7 Hz, 1H, C$\underline{H}$-CH$_3$), 4.35 (q; J=7 Hz, 2H, C$\underline{H}$-CH$_3$), 2.04 (d,J=7 $\overline{H}$z, 3H, CH-C$\underline{H}_3$), 1.50 (s; 9H, $\overline{C(CH_3)_3}$), 1.36 (t; J=7 Hz, 3H, CH$_2$-C$\underline{H}_3$).

E isomer:

$^1$H-NMR (250 MHz, $CDCl_3$): $\delta = 10.5$ (bs; 1H, NH), 7.22 (q; J=7 Hz, 1H, C$\underline{H}$-CH$_3$), 6.94 (s; 1H, S-CH), 4.19 (q; J=7 Hz, 2H, CH$_2$-C$\underline{H}_3$), 1.95 (d; J=7 Hz, 3H, CH-C$\underline{H}_3$), 1.52 (s; 9H, $\overline{C}(CH_3)_3$), 1.22 (t; J=7 Hz, 3H, CH$_2$-C$\underline{H}_3$).

EXAMPLE 9

Ethyl 2-(2-tert.-butoxycarbonylaminothiazol-4-yl)-2(E,Z)-benzylideneacetate 3.86 g (0.01 mol) of ethyl 2-tert.-butoxycarbonylimino-3-tert.-butoxycarbonyl-4-thiazolin-4-ylacetate in 40 ml of anhydrous tetrahydrofuran are colled down to −50°, 2.8 g (0.024 mol) of potassium tert.-butylate are added, the mixture is stirred until solution is complete and 1.11 ml (0.012 mol) of benzaldehyde is added. The mixture is allowed to warm to room temperature and is stirred overnight.

To work up, about 12 ml of 2N HCl are added with cooling in ice and monitoring the pH, until a pH of 4–5 is reached, the tetrahydrofuran and then the tert.-butanol are removed in vacuo and the residue is extracted with methylene chloride. After drying over $Na_2SO_4$, the methylene chloride is removed in vacuo. 3.1 g of an oil is obtained, which, according to NMR and TLC (cyclohexane/ether 1:1), is an approximately 1:1 mixture of E/Z isomers.

EXAMPLE 10

1-(2-tert.-Butoxycarbonylaminothiazol-4-yl)-1-(Z)-propenecarboxylic acid 0.145 mol (56 g) of ethyl 2-tert.-butoxycarbonylimino-3-tert.-butoxycarbonyl-4-thiazolin-4-ylacetate and 400 ml of anhydrous tetrahydrofuran are initially introduced under nitrogen and, at −60° to −50° C., 0.16 mol of n-butyllithium in hexane (15% strength, 100 ml) is added dropwise. Then 9.55 ml (0.17 mol) of acetaldehyde is immediately added, the mixture is stirred for 10 minutes at −60° C. and then overnight at room temperature.

Then 250 ml of 2N sodium hydroxide solution is added and the two-phase mixture is vigorously stirred at room temperature for 24 hours. The tetrahydrofuran is then distilled off at room temperature in vacuo and the alkaline phase is extracted twice with 100 ml of methylene chloride each time. After acidification of the aqueous phase to pH 2–3 and extraction, the 1-(2-tert.-butoxycarbonylaminothiazol-4-yl)-1(E)-propenecarboxylic acid is obtained (21.0 g, 51%, melting point=195° C. (from acetonitrile)).

The methylene chloride phase is concentrated in vacuo, the residue is taken up in 250 ml of ethanol, this is treated with 250 ml of 2N sodium hydroxide solution and heated at 60° C. for 24 hours.

After removal of the ethanol by distillation, the alkaline phase is extracted once with 100 ml of methylene chloride, the extract is discarded, the alkaline phase is acidified to pH 2–3 and the desired 1-(2-tert.-butoxycarbonylaminothiazol-4-yl)-1(Z)-propenecarboxylic acid is extracted with methylene chloride (8.3 g, 20%, melting point=183° C. (from acetonitrile)).

EXAMPLE 11

1-(2-tert.-Butoxycarbonylaminothiazol-4-yl)-1(Z)-butenecarboxylic acid

Preparation in analogy to Example 10 with propanal instead of acetaldehyde (yield 17%, melting point 172° C. from acetonitrile).

EXAMPLE 12

1-(2-tert.-butoxycarbonylaminothiazol-4-yl)-1(Z)-pentenecarboxylic acid

Preparation in analogy to Example 10 with butanal instead of acetaldehyde (melting point 162°–3° C., from acetonitrile).

EXAMPLE 13

1-(2-tert.-Butoxycarbonylaminothiazol-4-yl)-1(Z)-hexenecarboxylic acid

Preparation in analogy to Example 10 with pentanal instead of acetaldehyde (melting point 158° C., from acetonitrile).

EXAMPLE 14

1-(2-tert.-Butoxycarbonylaminothiazol-4-yl)-1(Z)-heptenecarboxylic acid

Preparation in analogy to Example 10 with hexanal instead of acetaldehyde (melting point 130°–1° C., from acetonitrile).

EXAMPLE 15

1-(2-tert.-Butoxycarbonylaminothiazol-4-yl)-1(Z)-octenecarboxylic acid

Preparation in analogy to Example 10 with heptanal instead of acetaldehyde (melting point 164° C., from acetonitrile).

EXAMPLE 16

1-(2-tert.-Butoxycarbonylaminothiazol-4-yl)-3-methyl-1(Z)-butenecarboxylic acid

Preparation in analogy to Example 10 with isobutyraldehyde instead of acetaldehyde (melting point 169°–71° C., from acetonitrile).

EXAMPLE 17

1-(2-tert.-Butoxycarbonylaminothiazol-4-yl)-4-methyl-1(Z)-pentenecarboxylic acid Preparation in analogy to Example 10 with isovaleraldehyde instead of acetaldehyde (melting point 173° C., from acetonitrile).

EXAMPLE 18

2-(2-tert.-Butoxycarbonylaminothiazol-4-yl)-3-cyclohexyl-(Z)-acrylic acid

Preparation in analogy to Example 10 with cyclohexyladehyde instead of acetaldehyde (melting point >210° C., from acetonitrile).

EXAMPLE 19

1-(2-tert.-Butoxycarbonylaminothiazol-4-yl)-4-phenyl-1(Z)-butenecarboxylic acid

Preparation in analogy to Example 10 with dihydrocinnamaldehyde instead of acetaldehyde (melting point 174° C., from acetonitrile).

EXAMPLE 20

1-(2-tert.-Butoxycarbonylaminothiazol-4-yl)-1(Z)-propenecarboxylic acid 0.43 mol (122 g) of 1-(2-tert.-butoxycarbonylaminothiazol-4-yl)-1(E)-propenecarboxylic acid in 800 ml of anhydrous tetrahydrofuran is treated with 0.52 mol (129 ml) of bistrimethylsilylacetamide and the mixture is stirred at room temperature for 1 hour. It is then cooled down to −60° C., 1.74 mols (200 g) of potassium tert.-butylate (98%) is added, the mixture is allowed to warm to room temperature and is stirred at room temperature overnight.

To work up, 100 ml of water is added while cooling in ice, the pH is adjusted to 6–8 with about 900 ml of 2N HCl, the tetrahydrofuran is removed in vacuo, the pH is adjusted to 2–3 and the mixture is extracted 3 times with 300 ml of methylene chloride. The extract is dried, concentrated on a rotary evaporator and the residue is dissolved in 700 ml of methanol. The methanolic solution is run through a column (2.5×80 cm; 400 ml) containing weakly basic ion exchanger Lewatit MP 62, at a rate of about 10 ml/minute, the column is washed with 2 l of methanol and eluted with 1 l of methanol/2N sodium hydroxide solution 10:1. The eluate is concentrated, acidified to pH 2–3 with 2N HCl and extracted with methylene chloride. After drying over $Na_2SO_4$ and distilling off the methylene chloride, 50 g (41%) of the desired Z-propenecarboxylic acid is obtained. The E-propenecarboxylic acid which did not isomerize is recovered from the column by evaporating the methanolic washings.

EXAMPLE 21

1-(2-tert.-Butoxycarbonylaminothiazol-4-yl)-1(Z)-penetenecarboxylic acid

By isomerization of the corresponding E-pentenecarboxylic acid in analogy to Example 20.
Yield 45%.

EXAMPLE 22

1-(2-tert.-Butoxycarbonylaminothiazol-4-yl)-1(Z)-propenecarboxylic methanesulphonic anhydride 0.005 mol (1.42 g) of 1-(2-tert.-butoxycarbonylaminothiazol-4-yl)-1(Z)-propenecarboxylic acid and 0.0055 mol (0.76 ml) of triethylamine are dissolved in 10 ml of anhydrous tetrahydrofuran and cooled down to −50° C. Then 0.0051 mol (0.40 ml) of methanesulphonyl chloride are added and the mixture is stirred at −40° to −50° C. for 5 hours. Then the triethylamine hydrochloride is filtered off under suction with exclusion of $H_2O$ and the tetrahydrofuran is distilled off in vacuo at −10° C. The mixed anhydride is obtained as an oil which readily isomerizes into the E form on warming (NMR).

EXAMPLE 23

1-(2-tert.-Butoxycarbonylaminothiazol-4-yl)-1(Z)-butenecarboxylic p-toluenesulphonic anhydride Preparation in analogy to Example 22 from the appropriate Z-butenecarboxylic acid and p-toluenesulphonyl chloride at −20° to −30° C.

EXAMPLE 24

7-[1-(2-tert.-Butoxycarbonylaminothiazol-4-yl)-1(Z)-propenecarboxamido]-3-acetoxymethyl-3-cephem-4-carboxylic acid 0.005 mol (1.42 g) of 1-(2-tert.-butoxycarbonylaminothiazol-4-yl)-1(Z)-propenecarboxylic acid and 0.0055 mol (0.76 ml) of triethylamine are dissolved in 20 ml of anhydrous methylene chloride, the mixture is cooled down to −50° C., 0.0051 mol (0.40 ml) of methanesulphonyl chloride is added and the mixture is stirred at −50° to −40° C. for 5 hours.

Then a solution of 0.006 mol (1.63 g) of 3-acetoxymethyl-7-amino-3-cephem-4-carboxylic acid and 0.013 mol (1.80 ml) of triethylamine in 20 ml of anhydrous methylene chloride, which has been previously cooled to −50° C., is added and the mixture is allowed to warm to room temperature over 12 hours.

To work up, the mixture is washed twice with 10 ml of $H_2O$ each time, the methylene chloride phase is covered with 40 ml of $H_2O$ and acidified, with stirring and cooling in ice, to pH 2–3 with 1N HCl. The organic phase is separated off, the $H_2O$ phase is extracted 2 times with 20 ml of methylene chloride each time, the combined methylene chloride phases are washed with saturated NaCl solution, dried over $Na_2SO_4$ and concentrated in vacuo on a rotary evaporator. The desired cephalosporin is obtained almost quantitatively.

EXAMPLE 25

7-[1-(2-tert.-Butoxycarbonylaminothiazol-4-yl)-1(Z)-propenecarboxamido]-3-(1-methyl-1H-tetrazol-5-yl)thiomethyl-3-cephem-4-carboxylic acid Preparation is carried out in analogy to Example 24 from 1-(2-tert.-butoxycarbonylaminothiazol-4-yl)-1(Z)-propenecarboxylic acid and 7-amino-3-(1-methyl-1H-tetrazol-5-yl)thiomethyl-3-cephem-4-carboxylic acid.
Yield 92%.

EXAMPLE 26

7-[1-(2-tert.-Butoxycarbonylaminothiazol-4-yl)-1(Z)-butenecarboxyamido]-3-acetoxymethyl-3-cephem-4-carboxylic acid Preparation in analogy to Example 24 from 1-(2-tert.-butoxycarbonylaminothiazol-4-yl)-1-(Z)-butenecarboxylic acid and 3-acetoxymethyl-7-amino-3-cephem-4-carboxylic acid.

EXAMPLE 27

7-[1-(2-tert.-Butoxycarbonylaminothiazol-4-yl)-1(Z)-butenecarboxamido]-3-(1-methyl-1H-tetrazol-5-yl)thiomethyl-3-cephem-4-carboxylic acid Preparation in analogy to Example 24 from 1-(2-tert.-butoxycarbonylaminothiazol-4-yl)-1(Z)-butenecarboxylic acid and 7-amino-3-(1-methyl-1H-tetrazol-5-yl)thiomethyl-3-cephem-4-carboxylic acid.
Yield 88%.

EXAMPLE 28

7-[1-(2-tert.-Butoxycarbonylaminothiazol-4-yl)-1(Z)-heptenecarboxamido]-3-acetoxymethyl-3-cephem-4-carboxylic acid Preparation in analogy to Example 24 from 1-(2-tert.-butoxycarbonylaminothiazol-4-yl)-1(Z)-heptenecarboxylic acid and 3-acetoxymethyl-7-amino-3-cephem-4-carboxylic acid.
Yield 90%.

EXAMPLE 29

7-[1-(2-tert.-Butoxycarbonylaminothiazol-4-yl)-1(Z)-heptenecarboxamido]-3-(1-methyl-1H-tetrazol-5-yl)-thiomethyl-3-cephem-4-carboxylic acid Preparation in analogy to Example 24 from 1-(2-tert.-butoxycarbonylaminothiazol-4-yl)-1(Z)-heptenecarboxylic acid and 7-amino-3-(1-methyl-1H-tetrazol-5-yl)thiomethyl-3-cephem-4-carboxylic acid. Yield 85%.

EXAMPLE 30

7-[1-(2-tert.-Butoxycarbonylaminothiazol-4-yl)-3-methyl-1(Z)-butenecarboxamido]-3-acetoxymethyl-3-cephem-4-carboxylic acid Preparation in analogy to Example 24 from 1-(2-tert.-butoxycarbonylaminothiazol-4-yl)-3-methyl-1(Z)-butenecarboxylic acid and 3-acetoxymethyl-7-amino-3-cephem-4-carboxylic acid.
Yield 93%.

EXAMPLE 31

7-[1-(2-tert.-Butoxycarbonylaminothiazol-4-yl)-4-phenyl-1(Z)-butenecarboxamido]-3-acetoxymethyl-3-cephem-4-carboxylic acid Preparation in analogy to Example 24 from 1-(2-tert.-butoxycarbonylaminothiazol-4-yl)-4-phenyl-1(Z)-butenecarboxylic acid and 3-acetoxymethyl-7-amino-3-cephem-4-carboxylic acid.
Yield 95%.

EXAMPLE 32

7-[1-(2-tert.-Butoxycarbonylaminothiazol-4-yl)-1(Z)-propenecarboxamido]-3-methyl-3-cephem-4-carboxylic acid Preparation in analogy to Example 24 from 1-(2-tert.-butoxycarbonylaminothiazol-4-yl)-1(Z)-propenecarboxylic acid and 7-amino-3-methyl-3-cephem-4-carboxylic acid. Unlike Example 24, the 7-amino-3-methyl-3-cephem-4-carboxylic acid is dissolved in methylene chloride with an equimolar amount of diisopropylamine instead of with triethylamine.

Yield 88%.

EXAMPLE 33

7-[1-(2-tert.-Butoxycarbonylaminothiazol-4-yl)-1(Z)-propenecarboxamido]-3-aminocarbonyloxymethyl-3-cephem-4-carboxylic acid Preparation in analogy to Example 24 from 1-(2-tert.-butoxycarbonylaminothiazol-4-yl)-1(Z)-propenecarboxylic acid and 7-amino-3-aminocarbonyloxymethyl-3-cephem-4-carboxylic acid. Unlike Example 24, the 7-amino-3-aminocarbonyloxymethyl-3-cephem-4-carboxylic acid is not dissolved in methylene chloride with triethylamine, but in anhydrous dimethylformamide with an equimolar amount of diisopropylamine, and the solution obtained is added to the mixed carboxylic sulphonic anhydride in methylene chloride.

To work up, the mixture is evaporated at 0° C. in vacuo, the residue is taken up in water, extracted with methylene chloride, the aqueous phase is covered with ethyl acetate and acidified to pH 2–3. The product separates out as an oil between the phases.

EXAMPLE 34

Diphenylmethyl
7-[1-(2-tert.-butoxycarbonylaminothiazol-4-yl)-1(Z)-propenecarboxamido]-3-cephem-4-carboxylate Preparation in analogy to Example 24 from 1-(2-tert.-butoxycarbonylaminothiazol-4-yl)-1(Z)-propenecarboxylic acid and diphenylmethyl 7-amino-3-cephem-4-carboxylate.

Yield 93%.

EXAMPLE 35

7-[1-(2-Aminothiazol-4-yl)-1(Z)-propenecarboxamido]-3-acetoxymethyl-3-cephem-4-carboxylic acid 10 ml of trifluoroacetic acid is added to the BOC-protected cephalosporin from Example 24, and the mixture is stirred at room temperature for 30 minutes. The trifluoroacetic acid is then removed at room temperature in vacuo, the residue is treated with 20 ml of methanol/$H_2O$ 10:1 and then with 10% strength $NaHCO_3$ solution, until a clear solution at pH 6–7 is obtained. The pH is then slowly adjusted to 3 with 1N HCl, the methanol is slowly removed in vacuo and, if necessary, the pH is adjusted again to 3. The precipitated product is filtered off under suction.

Yield 70%.

EXAMPLES 36–44

The cephalosporins from the Examples 25 to 34 are unblocked in analogy to Example 35.

Yields are between 50 and 90%.

It is understood that the specification and examples are illustrative but not limitative of the present invention and that other embodiments within the spirit and scope of the invention will suggest themselves to those skilled in the art.

I claim:

1. A compound of the formula $$R^3O-CO-N=\underset{\underset{R^3}{\overset{|}{O}}}{\underset{|}{\overset{|}{CO}}}\underset{N}{\overset{S}{\diagup}}\diagdown CO_2R^4$$

in which $R^3$ and $R^4$ each independently is an optionally substituted alkyl radical with 1 to 15 carbon atoms, an optionally substituted alkenyl radical with 3 to 15 carbon atoms, an optionally substituted cycloalkyl radical with 3 to 10 carbon atoms, an optionally substituted cycloalkenyl radical with 5 to 10 carbon atoms, an optionally substituted carbocyclic aryl radical with 1 to 3 rings or an optionally substituted heterocyclyl radical with 1 to 3 rings which can contain up to 5 heteroatoms selected from nitrogen, sulphur and oxygen, the optional substituents on the alkyl, alkenyl, cycloalkyl and cycloalkenyl radicals being alkyl or alkoxy with 1 to 4 carbon atoms, halogen, optionally substituted phenyl, CN and/or tri-($C_1$ to $C_5$ alkyl)-silyl, the optional substituents on the aryl and heterocyclyl radicals being alkyl, alkoxy, alkylthio and/or alkoxycarbonyl with 1 to 4 carbon atoms per alkyl goup, halogen, phenyl, nitro and/or CN.

2. A compound according to claim 1, in which $R^3$ both are $C(CH_3)_3$.

3. A compound according to claim 2, in which $R^4$ is a methyl or ethyl radical.

4. A compound according to claim 1, wherein such compound is ethyl 2-tert.-butoxycarbonylimino-3-tert.-butoxycarbonyl-4-thiazolin-4-ylacetate.

5. A process for the production of a compound according to claim 1, comprising reacting a thiazole derivative of the formula $$NH_2-\underset{N}{\overset{S}{\diagup}}\diagdown CO_2R^4$$

with a pyrocarbonic acid ester of the formula $$R^3-O-CO-O-CO-O-R^3$$

in a solvent for the reactants.

6. A process according to claim 5, in which the solvent is an aprotic polar solvent.

7. A process according to claim 5, in which the reaction is carried out at a temperature between about room temprature and −50° C.

8. A process according to claim 5, in which the pyrocarbonic acid ester is employed in about 2 to 2.5 mol-equivalents relative to the thiazole derivative.

* * * * *

UNITED STATES PATENT AND TRADEMARK OFFICE
CERTIFICATE OF CORRECTION

PATENT NO. : 4,500,716
DATED : February 19, 1985
INVENTOR(S) : Günther Kinast

It is certified that error appears in the above-identified patent and that said Letters Patent is hereby corrected as shown below:

1st page, Abstract, formula (XIII), delete beginning of formula and substitute:

line 6 from bottom delete "ae" and substitute --are--.

Col. 14, line 40   Correct spelling of "cooled"
Col. 15, line 8    Delete "(E)" and substitute --(E̲)--
Col. 15, line 20   Delete "(Z)" and substitute --(Z̲)--
Col. 16, line 65   Correct spelling of "pentenecarboxylic"

Signed and Sealed this

Fifth Day of November 1985

[SEAL]

Attest:

Attesting Officer

DONALD J. QUIGG

Commissioner of Patents and Trademarks